(12) United States Patent
Musa

(10) Patent No.: US 8,993,698 B2
(45) Date of Patent: *Mar. 31, 2015

(54) 4- AND 5 SUBSTITUTED 1,2,3-TRIAZOLE MOIETIES WITH AT LEAST ONE REMOTE POLYMERIZABLE MOIETY AND POLYMERS THEREOF

(75) Inventor: Osama M. Musa, Kinnelon, NJ (US)

(73) Assignee: ISP Investments Inc., Wilmington, DE (US)

( * ) Notice: Subject to any disclaimer, the term of this patent is extended or adjusted under 35 U.S.C. 154(b) by 217 days.

This patent is subject to a terminal disclaimer.

(21) Appl. No.: 13/382,975

(22) PCT Filed: Jul. 7, 2010

(86) PCT No.: PCT/US2010/041128
§ 371 (c)(1),
(2), (4) Date: Feb. 23, 2012

(87) PCT Pub. No.: WO2011/005806
PCT Pub. Date: Jan. 13, 2011

(65) Prior Publication Data
US 2012/0142846 A1    Jun. 7, 2012

Related U.S. Application Data

(60) Provisional application No. 61/223,991, filed on Jul. 8, 2009.

(51) Int. Cl.
| | |
|---|---|
| *C08F 220/34* | (2006.01) |
| *C07D 249/04* | (2006.01) |
| *C08F 26/06* | (2006.01) |
| *C08F 271/02* | (2006.01) |
| *C07D 249/06* | (2006.01) |
| *C08F 222/22* | (2006.01) |
| *C08F 226/06* | (2006.01) |

(52) U.S. Cl.
CPC .............. *C07D 249/04* (2013.01); *C08F 26/06* (2013.01); *C08F 271/02* (2013.01); *C07D 249/06* (2013.01); *C08F 220/34* (2013.01); *C08F 222/22* (2013.01); *C08F 226/06* (2013.01)
USPC ............................ 526/261; 548/255; 526/260

(58) Field of Classification Search
CPC .... C07D 249/04; C07D 249/06; C08F 26/06; C08F 271/02; C08D 139/04
USPC .................................. 548/255; 526/260, 261
See application file for complete search history.

(56) References Cited

U.S. PATENT DOCUMENTS

| | | | |
|---|---|---|---|
| 3,910,895 A | 10/1975 | Weber et al. | |
| 5,444,135 A * | 8/1995 | Cheradame et al. | ........ 526/219.2 |
| 2005/0222427 A1 | 10/2005 | Sharpless et al. | |
| 2006/0111530 A1* | 5/2006 | Li et al. | ......................... 526/258 |
| 2008/0266518 A1* | 10/2008 | Niu | ................................. 351/153 |
| 2008/0266519 A1* | 10/2008 | Schlueter | .................. 351/160 R |
| 2009/0171008 A1 | 7/2009 | Cracium | |
| 2012/0041040 A1* | 2/2012 | Musa et al. | .................... 514/359 |

OTHER PUBLICATIONS

Dubois, Propellants, Explosives, Pyrotechnics, vol. 28, Issue 3, 2003, p. 107-113.*
Jin, European Polymer Journal, 44 (2008) 1743-1751.*
Li, Journal of Polymer Science Part A: Polymer Chemistry, vol. 45, Issue 18, p. 4300-4308, 2007.*
Extended European Search Report dated Nov. 1, 2013.
Hunaid Nulwala et al: "Synthesis and Characterization of Isomeric Vinyl-1,2,3-triazole Materials by Azide-Alkyne Click Chemistry", Macromolecules, American Chemical Society, Washington, DC; US, vol. 42, No. 16, Aug. 25, 2009.
Zhen Zhou: "Development of Polymer Electrolyte Membranes for Fuel Cells to Be Operated At High Temperature and Low Humidity", Dissertation Presented to the Academic Faculty in Partial Fulfillment of the Requirements for the Degree Doctor of Philosophy in the School of Chemistry and Biochemistry, Georgia Institute of Technolo , Apr. 9, 2007, pp. I-XIII,1, XP008150024, Retrieved from the Internet: URL:http://smartech.gatech.edu/handle/1853/22559.
Sobhani A M et al: "A theory of mode of action of azolylalkylquinolines as DNA binding agents using automated flexible ligand docking", Journal of Molecular Graphics and Modelling, Elsevier Science, New York, NY, US, vol. 25, No. 4, Dec. 1, 2006.

Michael J. Ellis et al: "Antitumour polycyclic acridines. Part 9.1 Synthesis of 7H-pyrido[4,3,2-kl]acridines with basic side chains", Journal of the Chemical Society, Perkin Transactions 1, No. 23, Nov. 29, 2001.

Maksikova A V et al: "[Synthesis of triazole and tetrazole ethers]", Izvestia Vyssih Ucebnyh Zavedenij. Himia I Himiceskaa Technologia, Sowjetunion Ministerstvo Vys Ego I Srednego Special'Nogo Obrazovanija, Russia, vol. 27, No. 2, Jan. 1, 1984.

P. Ykman et al: "Reactions of vinyl azides with .alpha.-oxo phosphorus ylides. Synthesis of N1-vinyltriazoles", The Journal of Organic Chemistry, vol. 37, No. 21, Oct. 1, 1972, pp. 3213-3216, XP055048173, ISSN: 0022-3263, DOI: 10.1021/jo00986a004.

G. L'Abbe: "Decomposition and addition reactions of organic azides", Chemical Reviews, vol. 69, No. 3, Jun. 1, 1969.

Khuseinov K et al: "[Acrylic and methacrylic monomers with a 1,2,3-triazole ring]", Izvestia Vyssih Ucebnyh Zavedenij. Himia I Himiceskaa Technologia, Sowjetunion Ministerstvo Vys Ego I Srednego Special'Nogo Obrazovanija, Russia, vol. Khimiya i Khimicheskaya Tekhnologiya, Jan. 1, 1976.

L'Abbé G et al: "Regiochemistry in Cycloaddition Reactions of Vinyl Azides with Phenylacetylene[1]", Bulletin Des Societes Chimiques Belges, Louvain [U.A.] : Centerick, BE, vol. 80, No. 1-2, Jan. 1, 1971, pp. 209-210, XP008158903, ISSN: 0037-9646, DOI: 10.1002/BSCB.19710800124 [retrieved on Sep. 2, 2010].

Journal of Chemical Crystallography, vol. 37, No. 1, Jan. 2007 "A new family of energetic ionic liquids 1-amino-3-alkyl-1,2,3-triazolium nitrates".

\* cited by examiner

*Primary Examiner* — Robert C Boyle

(74) *Attorney, Agent, or Firm* — William J. Davis

(57) ABSTRACT

The present invention provides novel 4- and 5-substituted 1,2,3-triazole moieties, with at least one remote polymerizable moiety. The novel mixtures of 4- and 5-substituted regioisomers of 1,2,3-triazole moieties can be separated by chromatography to provide the purified 4- and 5-substituted 1,2,3-triazole moieties. The novel mixtures of 4- and 5-substituted regioisomers of 1,2,3-triazole moieties, and the purified 4- and 5-substituted 1,2,3-triazole moieties, with at least one remote polymerizable moiety, can be converted to a wide variety of useful polymers. The novel compounds of the invention can be employed in a wide variety of compositions. E, Q, Z, X, a, and $R_1$-$R_4$, in the structures below, are defined herein.

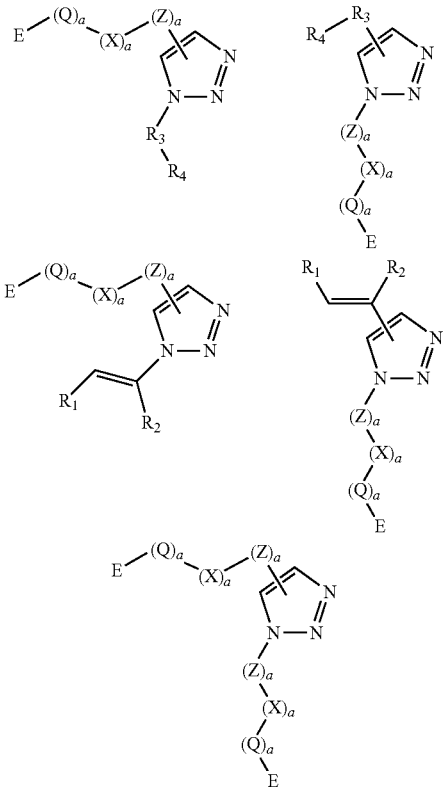

1 Claim, 4 Drawing Sheets

4- AND 5 SUBSTITUTED 1,2,3-TRIAZOLE MOIETIES WITH AT LEAST ONE REMOTE POLYMERIZABLE MOIETY AND POLYMERS THEREOF

BACKGROUND OF THE INVENTION

1. Field of the Invention

The present invention provides novel 4- and 5-substituted 1,2,3-triazole moieties, with at least one remote polymerizable moiety. The novel compounds are prepared by the ligation of azides and alkynes using 1,3-dipolar cycloaddition reactions. Alkyne moieties with a terminal reactive functionality are reacted with organic moieties with a terminal leaving group and an azide to provide a mixture of 4- and 5-substituted regioisomers of 1,2,3-triazole moieties. A remote polymerizable moiety may be present in the alkyne moiety, the organic moiety, or the azide, or mixtures thereof, to provide a mixture of 4- and 5-substituted regioisomers of 1,2,3-triazole moieties, with at least one remote polymerizable moiety. The mixture may also then be reacted with a precursor to a polymerizable moiety to provide a wide variety of useful mixtures of 4- and 5-substituted regioisomers of 1,2,3-triazole moieties, with at least one remote polymerizable moiety. The novel mixtures of 4- and 5-substituted regioisomers can be separated by chromatography to provide the purified 4- and 5-substituted 1,2,3-triazole moieties. The novel mixtures of 4- and 5-substituted regioisomers of 1,2,3-triazole moieties, and the purified 4- and 5-substituted 1,2,3-triazole moieties, with at least one remote polymerizable moiety, can be converted to a wide variety of useful polymers. The novel compounds of the invention can be employed in a wide variety of compositions.

2. Description of Related Art

The ligation of azides and alkynes using a 1,3-dipolar cycloaddition reaction (azide/alkyne chemistry) has been described in United States patent application 2005/0222427 and in EP patent 1507769. The reaction involves ligation of azides and alkynes in solution using a copper (I) salt catalyst [Cu(I)], or a copper (II) salt catalyst [Cu(II)] in the presence of a reducing agent, such as sodium ascorbate, to provide triazole polymer moieties under ambient conditions ("click reaction"), see H. C. Kolb, M. G. Finn and K. B. Sharpless, *Angew. Chem. Int. Ed.* 2001, 40, 2004-2021. The advantage of the copper catalyzed method over the uncatalyzed method is said to be rate acceleration and exclusive 1,4-regioselectivity. These references also describe azide/alkyne ligation chemistry for the preparation of triazole polymer moieties as metal adhesives using Cu(I) catalysts, prepared by reducing Cu(II) or by oxidizing copper metal to Cu(I) in situ, see D. D. Diaz, S. Punna, P. Holzer, A. K. McPherson, K. B. Sharpless, V. V. Fokin, M. G. Finn, *J. Polym. Sci: Part A: Polym. Chem.* 2004, 42, 4392-4403. References that describe the preparation of vinyl-1,2,3-triazole moieties include G. Wouters, et al., *Makromol. Chem.* 183 1861-1868 (1982); Raymond J. Thibault, et al., *J. Am. Chem. Soc.* 2006, 128, 12084-120585; and Kenichi Takizawa, et al., *J. of Polym. Sci.: Part A: Polym. Chem.*, Vol. 46, 2897-2912 (2008).

The copper catalyzed azide/alkyne chemistry requires relatively mild reaction conditions that are not sensitive to air or moisture in contrast to the conditions used in radical polymerizations that are often inhibited by oxygen, leading to incomplete polymerization and reduced yield. Nevertheless, the copper catalyzed azide/alkyne chemistry reactions require the disposal of the catalyst and/or solvent, which adds steps to the synthetic method. It would advantageous to have a method that did not require removal of a catalyst or organic solvent. It would be advantageous also to have a method to prepare 1,2,3-triazole moieties with new polymerizable moieties. Such a method would be useful whether the 1,2,3-triazole moieties are prepared with or without a catalyst.

SUMMARY OF THE INVENTION

The present invention provides a wide variety of mixtures of 4- and 5-substituted regioisomers of 1,2,3-triazole moieties and purified 4- and 5-substituted 1,2,3-triazole moieties, all with at least one remote polymerizable moiety.

The mixtures of 4- and 5-substituted regioisomers of 1,2,3-triazole moieties and purified 4- and 5-substituted 1,2,3-triazole moieties can be converted to homopolymers of mixtures of 4- and 5-substituted regioisomers of 1,2,3-triazole moieties, purified homopolymers of 4- and 5-substituted 1,2,3-triazole moieties, non-homopolymers of mixtures of 4- and 5-substituted regioisomers of 1,2,3-triazole moieties, and purified non-homopolymers of 4- and 5-substituted 1,2,3-triazole moieties, respectively, each with at least one remote polymerizable moiety. The above non-homopolymers may be random, blocked, or alternating polymers. The present invention also provides adhesive, coating, encapsulation, personal care, oilfield, membrane, agricultural, and cleaning compositions comprising the above substituted 1,2,3-triazole moieties.

In one embodiment, the present invention provides a mixture of 4- and 5-substituted regioisomers of 1,2,3-triazole moieties with at least one remote polymerizable moiety including compounds represented by the structures:

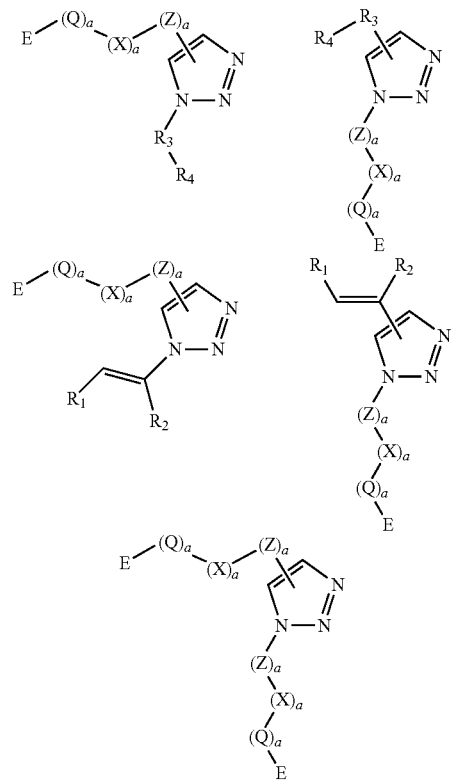

wherein E is a remote polymerizable reactant moiety independently selected from the group consisting of anhydrides, vinyl amides, acrylates, styrenes, maleimides, maleates, fumarates, cinnamyls, vinyl imidazoles, vinyl pyridines, vinyl acetates, acrylamides, vinyl sulfones, vinyl carbonates, vinyl silanes, vinyl actylamides, allyl derivatives, vinyl ethers, epoxies, oxetanes, benzoxazines, oxazolines, and mixtures thereof; Q and Z are independently selected from the group consisting of funetionalized and unfunctionalized alkyl, cycloalkyl, alkenyl, and aryl groups, wherein any of the before mentioned groups may be with or without heteroatoms, and mixtures thereof; X is a linker group selected from the group consisting of carbamates, ureas, amides, esters, ethers, ketones, amines, sulfides, disulfides, thiocarbamates, and mixtures thereof; a is 0 or 1; $R_1$, $R_2$, and $R_3$ are independently selected from the group consisting of hydrogen, functionalized and unfunctionalized alkyl, cycloalkyl, alkenyl, and aryl groups, wherein any of the before mentioned groups may be with or without heteroatoms; and $R_4$ is selected from the group consisting of a direct bond, carboxylic acids, esters, amides, anhydrides, aldehydes, ketones, ethers, amines, alcohols, thiols, and mixtures thereof, with the proviso that when $R_3$ is hydrogen, $R_4$ is a direct bond.

In another embodiment, the present invention provides a 4-substituted 1,2,3-triazole moiety with at least one remote polymerizable moiety including compounds represented by the structures:

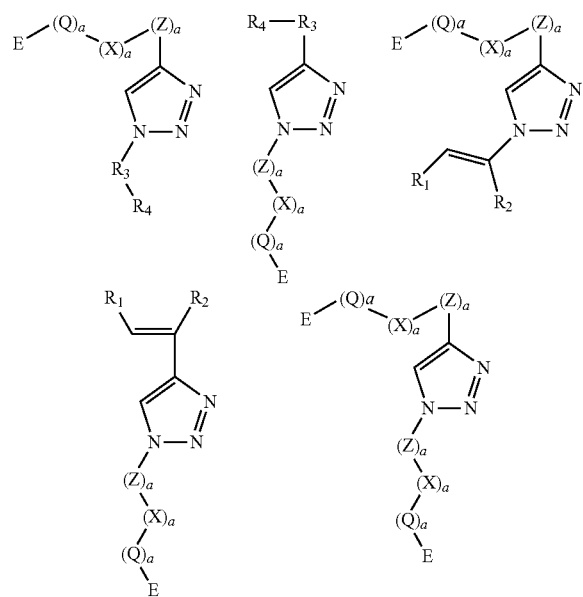

wherein E, Q, Z, X, a, and $R_1$-$R_4$ are as defined above.

In another embodiment, the present invention provides a 5-substituted 1,2,3-triazole moiety with at least one remote polymerizable moiety including compounds represented by the structures:

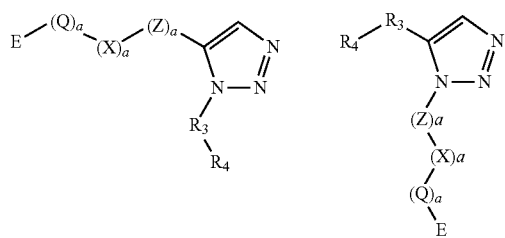

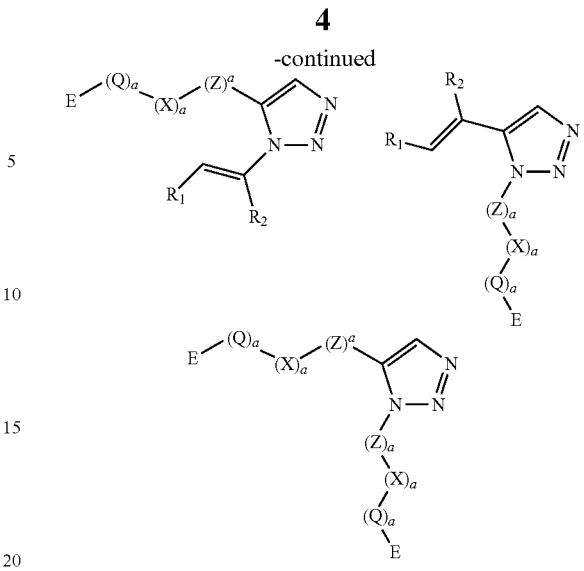

wherein E, Q, Z, X, a, and $R_1$-$R_4$ are as defined above.

DETAILED DESCRIPTION OF PREFERRED EMBODIMENTS

Figure 1:
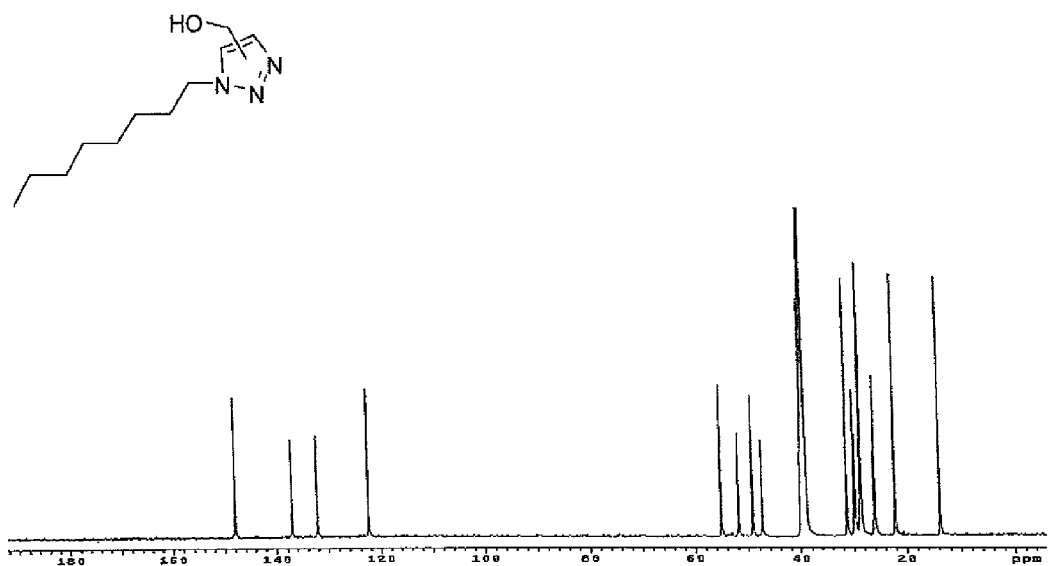
FIG. 1 is an NMR spectrum for compounds produced in accordance with Example 1.

The present invention provides a new monomer family with at least one remote polymerizable moiety, which combines the desirable features of thermal and chemical stability while providing functional versatility. Triazole monomers with at least one remote polymerizable moiety are a significant advance beyond classic vinyl monomers derived from styrenic, acrylate, or α-olefin-based monomer systems. The invention demonstrates the utility of cycloaddition of azides and alkynes resulting in unique triazole monomers. This utility is supported by the benign (environmentally friendly) character of cycloaddition reaction conditions, functional group tolerance, quantitative yields and relevance to a broad range of applications. These applications encompass adhesive, coating, encapsulation, personal care, oilfield, membrane, agricultural, and cleaning compositions. As found in styrenics, vinyl pyridines, and acrylates, the 1,2,3-triazole moieties with at least one remote polymerizable moiety of the present invention possess attractive features including stability, aromaticity, polarity, and versatility with substitutions at N–1. This new monomer family may be employed to yield novel triazole homopolymers and non-homopolymers, reacted with a comonomer (different polymerizable reactant moiety). The new monomer family with at least one remote polymerizable moiety also may contain a second remote polymerizable moiety or a non-remote polymerizable moiety.

As used herein, the following terms have the meanings set out below.

The term "remote polymerizable moiety" refers to a polymerizable moiety that is not directly connected covalently to the 1,2,3-triazole ring moiety. A remote polymerizable moiety is distal or remote from the 1,2,3-triazole ring moiety. In the structure set out below, because of the definitions of $(Q)_a$, $(X)_a$, and $(Z)_a$ (with the proviso that each "a" is not zero at the same time), E is a remote polymerizable moiety because it is not directly connected covalently to the 1,2,3-triazole ring moiety.

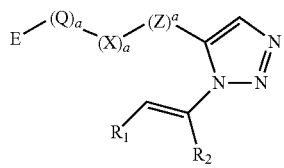

The term "non-remote polymerizable moiety" refers to a polymerizable moiety that is directly connected covalently to the 1,2,3-triazole ring moiety. In the structure set out below, because the vinyl group, with the $R_1$ and $R_2$ groups, is directly connected covalently to the 1,2,3-triazole moiety, the vinyl group is a non-remote polymerizable moiety.

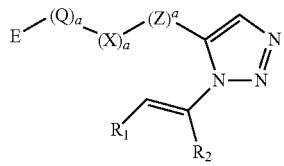

The configuration of the $R_1$ and $R_2$ groups on the vinyl bond is not meant to suggest any particular type of stereoisomerism about the double bond. Traditionally, double bond stereochemistry was described as either cis (on this side) or trans (across), in reference to the relative position of substituents on either side of the double bond. IUPAC adopted a more rigorous system wherein the substituents at each end of the double bond are assigned priority based on their atomic number. If the high priority substituents are on the same side of the double bond, the compound is assigned Z (zusantinen, together). If the high priority substituents are on opposite sides, the compound is assigned E (entgegen, opposite). In the present invention, the structure of the vinyl substituted 1,2,3-triazole moiety referred to in the example below can be in either the E or Z configuration, or mixtures thereof.

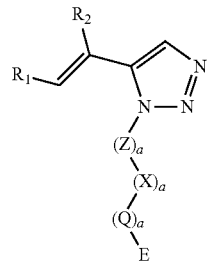

The term "alkyne moiety" refers to an alkyne group, which may be attached to an unsubstituted or substituted alkyl, cycloalkyl, alkenyl, and aryl groups, wherein any of the before mentioned groups may be present with or without heteroatoms. The alkyl and alkenyl groups may be branched or unbranched (straight-chain). Preferably, the alkyl and alkenyl groups are $C_1$-$C_{60}$, more preferably $C_1$-$C_{36}$, and most preferably $C_1$-$C_{18}$ groups. Cycloalkyls (closed rings) include cyclopentane, cyclohexane, cycloheptane, and the like. Aryl groups include benzenes, naphthalenes (2 rings), and anthracenes (3 rings), and the like.

The symbol of a "bond to the middle of a vinyl group" means that the bond can be attached to either side of the vinyl group and means that the structure is referring to a mixture of isomers. For example, in the structure below:

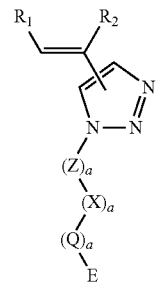

the vinyl group containing $R_1$ and $R_2$ can be attached to either the 4 or the 5 position of the 1,2,3-triazole moiety.

The term "comonomer" refers to a polymerizable reactant moiety different from the 4- and 5-substituted 1,2,3-triazole moieties of the invention (different polymerizable reactant moiety) so that when the two are reacted, non-homopolymers are obtained.

The term "direct bond" means that the group can be nothing.

The term "free radical addition polymerization initiator" refers to a compound used in a catalytic amount to initiate a free radical addition polymerization. The choice of initiator depends mainly upon its solubility and its decomposition temperature.

The term "mixture of 4- and 5-substituted regioisomers of 1,2,3-triazole moieties with at least one remote polymerizable moiety" refers to mixtures of 1,2,3-triazole moieties substituted with a group at the 4 and 5-position on the 1,2,3-triazole. Some non-limiting examples of structures of functionalized mixtures of 4- and 5-substituted regioisomers of 1,2,3-triazole moieties include:

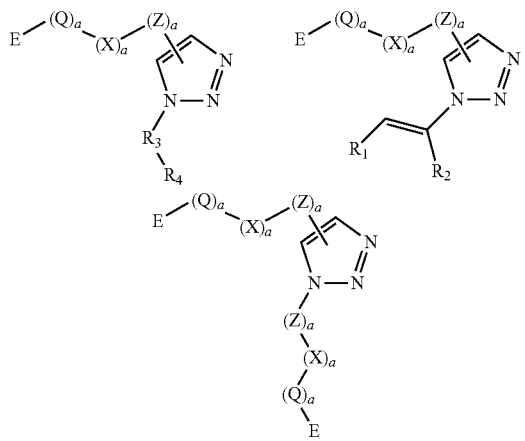

The term "halogen" refers to chloro, bromo, iodo and fluoro, and is preferably bromo or chloro.

The term "heteroatom" refers to atoms such as oxygen, nitrogen, sulfur, and phosphorous.

The term "homopolymer" refers to a polymer formed from a single monomer.

The term "inert solvent" refers to a solvent that does not interfere chemically with the reaction.

The term "leaving group" refers to any group that can be displaced by an azide ion. Nonlimiting examples include halogens, silyl groups, tosyl groups, and mesyl groups.

The term "ligation" refers to an act of uniting or connecting two or more starting materials or reactants.

The term "non-homopolymer" refers to a polymer formed from two or more different monomers and includes essentially all polymers that are not homopolymers. Nonlimiting examples of non-homopolymers include copolymers, terpolymers, tetramers, and the like, wherein the non-homopolymer is a random, blocked, or alternating polymer.

The terms "mixture of 4- and 5-substituted regioisomers of 1,2,3-triazole moieties with at least one remote polymerizable moiety", "4-substituted 1,2,3-triazole moiety with at least one remote polymerizable moiety", and "5-substituted 1,2,3-triazole moiety with at least one remote polymerizable moiety" refer to substituted 1,2,3-triazole moieties having, for example, respectively the structures shown below:

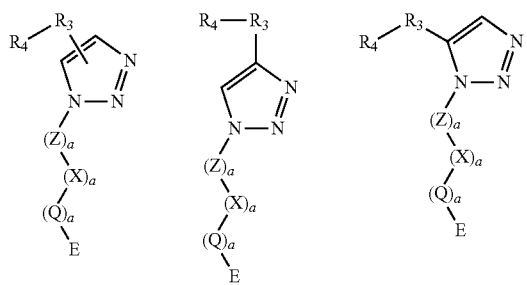

The term "monomer" refers to the repeat units comprising a polymer. A monomer is a small molecule that chemically bonds to other monomers to form a polymer.

The term "organic moiety" refers to an unsubstituted or substituted alkyl, cycloalkyl, alkenyl, and aryl groups, wherein any of the before mentioned groups may be present with or without heteroatoms. The alkyl and alkenyl groups may be branched or unbranched (straight-chain). Preferably, the alkyl and alkenyl groups are $C_1$-$C_{60}$, more preferably $C_1$-$C_{36}$, and most preferably $C_1$-$C_{18}$ groups. Cycloalkyls (closed rings) include cyclopentane, cyclohexane, cycloheptane, and the like. Aryl groups include benzenes, naphthalenes (2 rings), and anthracenes (3 rings), and the like.

The term "personal care composition" refers to such illustrative non-limiting compositions as skin, sun, oil, hair, cosmetic, and preservative compositions, including those to alter the color and appearance of the skin. Potential personal care compositions include, but are not limited to, polymers for increased flexibility in styling, durable styling, increased humidity resistance for hair, skin, and color cosmetics, sun care water-proof/resistance, wear-resistance, and thermal protecting/enhancing compositions.

The term "polymer" refers to a large molecule (macromolecule) composed of repeating structural units (monomers) connected by covalent chemical bonds.

As set out above, the present invention provides a new monomer family, with at least one remote polymerizable moiety. This new monomer family may be employed to yield novel triazole homopolymers and non-homopolymers, which are useful in a wide variety of applications. These applications include adhesive, coating, encapsulation, personal care, oilfield, membrane, agricultural, and cleaning compositions. The new monomer family with at least one remote polymerizable moiety also may contain a second remote polymerizable moiety or a non-remote polymerizable moiety.

The synthesis of the functionalized mixtures of 4- and 5-substituted regioisomers of 1,2,3-triazole moieties, with at least one remote polymerizable moiety, occur in solution and lead to the desired N-1 functionalized mixtures of 4- and 5-substituted regioisomers of 1,2,3 triazole moieties. The novel compounds are prepared by the ligation of azides and alkynes using 1,3-dipolar cycloaddition reactions. Alkyne moieties with a terminal reactive functionality are reacted with organic moieties with a terminal leaving group and an azide to provide a mixture of 4- and 5-substituted regioisomers of 1,2,3-triazole moieties. A remote polymerizable moiety may be present in the alkyne moiety, the organic moiety, or the azide, or mixtures thereof, to provide a mixture of 4- and 5-substituted regioisomers of 1,2,3-triazole moieties, with at least one remote polymerizable moiety. The mixture may also then be reacted with a precursor to a polymerizable moiety to provide a wide variety of useful mixtures of 4- and 5-substituted regioisomers of 1,2,3-triazole moieties, with at least one remote polymerizable moiety. The novel mixtures of 4- and 5-substituted regioisomers can be separated by chromatography to provide the purified 4- and 5-substituted 1,2,3-triazole moieties. The novel mixtures of 4- and 5-substituted regioisomers of 1,2,3-triazole moieties, and the purified 4- and 5-substituted 1,2,3-triazole moieties, with at least one remote polymerizable moiety, can be converted to a wide variety of useful polymers. The novel compounds of the invention can be employed in a wide variety of compositions. The 4- and 5-substituted 1,2,3-triazole moieties of the present invention, with at least one remote polymerizable moiety, may also be prepared by catalyzed methods, which provide a single isomer.

The alkyne moiety may be an unsubstituted or substituted alkyl, cycloalkyl, alkenyl, and aryl groups, wherein any of the before mentioned groups may be present with or without heteroatoms. Preferably, the alkyne moiety is selected from the group consisting of 2-methyl-3-butyn-2-ol, propargyl alcohol, but-3-yn-2-ol, 3,6-dimethyl-4-octyne-3,6-diol, 1-phenyl-1-hexyn-3-ol, 1-phenyl-4-methyl-1-pentyn-3-ol, 7-methoxy-3,7-dimethyl-oct-1-yn-3-ol, 3,8 dihydroxy-3,8-dimethyl-4,6-decadiyne, 1-trimethylsilanylethynyl-cyclohexanol, 1-phenyl-3-pentyn-2-ol, 4-bromo-2-methyl-3-butyn-2-ol, 2-(2-fluorophenyl)-3-butyn-2-ol, 244-fluorophenyl)-3-butyn-2-ol, 2-(3-fluorophenyl)-3-butyn-2-ol, 2,7-dimethyl-3,5-octadiyne-2,7-diol, 2,6-dimethyl-oct-2-en-7-yne-1,6-diol, (S)-(−)-3-butyn-2-ol, ®-(+)-3-butyn-2-ol, and 3-pentyn-2-ol. More preferably, the alkyne moiety is 2-methyl-3-butyn-2-ol.

The organic moiety with a terminal leaving group may be an unsubstituted or substituted alkyl, cycloalkyl, alkenyl, and aryl groups, wherein any of the before mentioned groups may be present with or without heteroatoms. Preferably, the organic moiety is selected from the group consisting of 1-bromooctane, methyl-3-bromopropionate, 2-chloroethanol, 2-(2 chloroethoxy)ethanol, (dimethylamino)ethylchloride, 3-chloro-1-propene, 2-chloroacetamide, acetyl chloride, 1-chloropropane, chloromethyl octyl ether, bromoethane, bromoacetonitrile, 3-bromo-1-pentene, 2-bromopropane, 3-bromofuran, and 2-bromoimidazole. More preferably, the organic moiety is selected from the group consisting of 1-bromooctane, methyl-3-bromopropionate, 2-chloroethanol, 2-(2-chloroethoxy)ethanol, and (dimethylamino)ethylchloride. An attractive feature of this synthetic approach is the versatility afforded by the wide variety of alkyllaryl halide starting reagents available. Thus, a wide variety of functionalized mixtures of 4- and 5-substituted regioisomers of 1,2,3-triazole moieties with various N-1 substituents can be readily obtained.

The terminal reactive functionality may be selected from the group consisting of carboxylic acids, esters, amides, anhydrides, aldehydes, ketones, ethers, amines, alcohols, thiols, and mixtures thereof. Preferably, the terminal reactive functionality is selected from the group consisting of carboxylic acids, amines, alcohols, thiols, and mixtures thereof.

In one embodiment, the terminal reactive functionality may be a terminal alcoholic functionality. In a first step, conditions for preparation of the triazole intermediate may be environmentally friendly. For example, the reaction of an alkyne moiety with a terminal alcoholic functionality, such as propargyl alcohol, sodium azide and an organic moiety with a terminal leaving group, such as bromo-octane, is carried out in an aqueous medium without catalyst(s). Following generation of the azide derivative (displacement of the leaving group by the azide ion), a triazole "nucleus" is formed (1,3 cycloaddition of the azide to the alkyne) and isolated as an alcoholic N-1 functionalized mixture of 4- and 5-substituted regioisomers of 1,2,3-triazole moieties. In the next step, the alcoholic N-1 functionalized mixture of 4- and 5-substituted regioisomers of 1,2,3-triazole moieties can then be reacted with a precursor to a precursor to a remote polymerizable moiety to provide the subject mixture of 4- and 5-substituted regioisomers of 1,2,3-triazole moieties with at least one remote polymerizable moiety. This reaction delivers a high yield of the desired N-1 substituted 4- and 5-substituted regioisomers of 1,2,3-triazole moieties.

The alcoholic mixture of 4- and 5-substituted regioisomers of 1,2,3-triazole moieties is preferably represented by the structure:

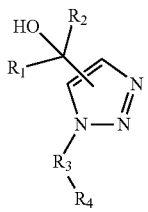

wherein $R_1$-$R_4$ are as defined above.

Preferably, the alcoholic functionalized mixture of 4- and 5-substituted regioisomers of 1,2,3-triazole moieties may be selected from the group consisting of

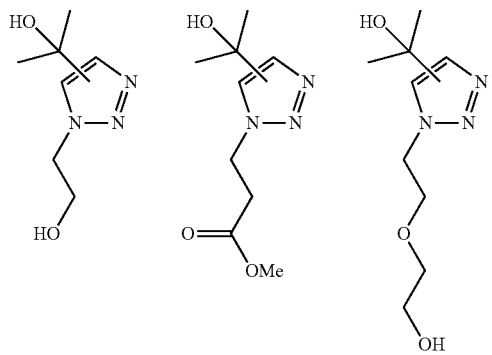

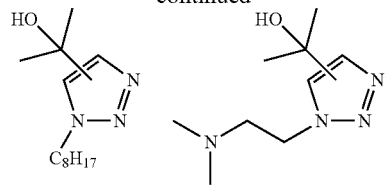

More preferably, the alcoholic functionalized mixture of 4- and 5-substituted regioisomers of 1,2,3-triazole moieties is:

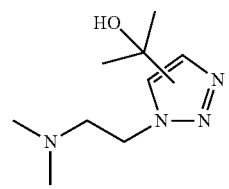

As set out above, the alcoholic functionalized mixture of 4- and 5-substituted regioisomers of 1,2,3-triazole moieties can then be reacted with a precursor to a remote polymerizable moiety to provide a mixture of 4- and 5-substituted regioisomers of 1,2,3-triazole moieties with at least one remote polymerizable moiety.

The remote polymerizable reactant moiety may be selected from the group consisting of anhydrides, vinyl amides, acrylates, styrenes, maleimides, maleates, fumarates, cinnamyls, vinyl imidazoles, vinyl pyridines, vinyl acetates, aciylamides, vinyl sulfones, vinyl carbonates, vinyl silanes, vinyl acrylamides, allyl derivatives, vinyl ethers, epoxies, oxetanes, benzoxazines, oxazolines, and mixtures thereof. Illustrative, non-limiting examples of anhydrides include maleic anhydride, phthalic anhydride, lauric anhydride, pyromellitic anhydride, trimellitic anhydride, hexahydrophthalic anhydride; hexahydropyromellitic anhydride, hexahydrotrimellitic anhydride, itaconic anhydrides, citraconic anhydrides, and mixtures thereof.

The novel mixtures of 4- and 5-substituted regioisomers of 1,2,3-triazole moieties, and the purified 4- and 5-substituted 1,2,3-triazole moieties, with at least one remote polymerizable moiety, may be employed in compositions having a wide variety of applications. Non-limiting illustrative examples of such compositions include adhesive, coating, encapsulation, personal care, oilfield, membrane, agricultural, and cleaning compositions. These moieties may be used in any industrial field. They are of particular use for electronic, electrical, opto-electronic, and photo-electronic applications. Such applications include die attach adhesives, underfill encapsulants, antennae for radio-frequency identification (RFID), via holes, film adhesives, conductive inks, circuit board fabrication, other laminate end uses, and other uses with printable electronics.

As set out above, the mixtures of 4- and 5-substituted regioisomers of 1,2,3-triazole moieties, and the purified 4- and 5-substituted 1,2,3-triazole moieties, with at least one remote polymerizable moiety, may be converted to a wide variety of useful polymers including homopolymers and non-homopolymers, reacted with a comonomer moiety. These polymers may also be employed in compositions having a wide variety of applications. The useful compositions are set out above for the 4- and 5-substituted 1,2,3-triazole moieties.

Because the method of the present invention does not employ a catalyst, the method provides functionalized mixtures of 4- and 5-substituted regioisomers of 1,2,3-triazole moieties. Copper catalyzed methods provide mainly the 4-substituted regioisomer. The mixtures of 4- and 5-substituted regioisomers may be separated by conventional chromatographic methods to provide the purified 4-substituted regioisomers and the 5-substituted regioisomers. The purified 4-substituted regioisomers and the 5-substituted regioisomers may then be employed to prepare 4- and 5-substituted homopolymers and non-homopolymers Chromatography is the collective term for a group of laboratory techniques for the separation of mixtures. The techniques involve passing a mixture dissolved in a mobile phase through a stationary phase, which separates the analyte to be measured from other molecules in the mixture and allows it to be isolated. Preparative chromatography, the preferred technique to be employed in this invention, separates the components of a mixture for further use and is thus a form of purification. The various forms of chromatography are well known to those of skill in the art. The most general technique for separating large amounts of material is column chromatography. Column chromatography is a separation technique in which the stationary bed is within a tube. The particles of the solid stationary phase or the support coated with a liquid stationary phase may fill the whole inside volume of the tube (packed column) or be concentrated on or along the inside tube wall leaving an open, unrestricted path for the mobile phase in the middle part of the tube. Differences in rates of movement through the medium are calculated to different retention times of the sample. Another technique that may be employed is liquid chromatography, which is a separation technique in which the mobile phase is a liquid. Liquid chromatography can be carried out either in a column or a plane. Liquid chromatography that generally utilizes very small packing particles and a relatively high pressure is referred to as high performance liquid chromatography (HPLC). In the HPLC technique, the sample is forced through a column that is packed with irregularly or spherically shaped particles or a porous monolithic layer (stationary phase) by a liquid (mobile phase) at high pressure. HPLC is generally divided into two different sub-classes based on the polarity of the mobile and stationary phases. The technique in which the stationary phase is more polar than the mobile phase is called normal phase liquid chromatography (HPLC) and the opposite is called reversed phase liquid chromatography (HPLC). Reversed-phase chromatography is an elution procedure used in liquid chromatography in which the mobile phase is significantly more polar than the stationary phase. The appropriate method and conditions of chromatography to separate the mixtures of 4- and 5-substituted regioisomers are well known in the art.

As set out above, the availability of various N-1 substituent options allows for the custom manufacturing of polymers with specific physical property properties. For example when the N-1 substituent is n-$C_8H_{17}$, one obtains a hydrophobic functionalized mixture of 4- and 5-vinyl substituted regioisomers of 1,2,3-triazole moieties. On the other hand, when the N-1 substituent is $CH_2CH_2OH$, $CH_2CH_2OCH_2CH_2OH$, or $CH_2CH_2N(CH_3)_2$, one obtains a hydrophilic functionalized mixture of 4- and 5-vinyl substituted regioisomers of 1,2,3-triazole moieties.

Optionally, a free radical addition polymerization initiator may be employed in the polymerization reaction. Non-limiting illustrative examples of free radical addition polymerization initiators include 2,2'-azobis (2-methylpropionitrile) and benzoyl peroxide. A preferred free radical addition polymerization initiator is 2,2'-azobis (2-methylpropionitrile).

Depending on the end application, one or more fillers may be included in the compositions and usually are added for improved rheological properties and stress reduction. Examples of suitable nonconductive fillers include alumina, aluminum hydroxide, silica, fused silica, fumed silica, vermiculite, mica, wollastonite, calcium carbonate, titania, sand, glass, barium sulfate, zirconium, carbon black, organic fillers, and halogenated ethylene polymers, such as, tetrafluoroethylene, trifluoroethylene, vinylidene fluoride, vinyl fluoride, vinylidene chloride, and vinyl chloride. Examples of suitable conductive fillers include carbon black, graphite, gold, silver, copper, platinum, palladium, nickel, aluminum, silicon carbide, boron nitride, diamond, and alumina.

The filler particles may be of any appropriate size ranging from nano size to several mm. The choice of such size for any particular end use is within the expertise of one skilled in the art. The filler may be present in an amount from 10% to 90% by weight of the total composition. More than one filler type may be used in a composition and the fillers may or may not be surface treated. Appropriate filler sizes can be determined by the practitioner, but, in general, will be within the range of 20 nanometers to 100 microns.

Other materials, such as adhesion promoters (e.g., epoxides, silanes), dyes, pigments, and rheology modifiers may be added as desired for the modification of the final properties. Such materials and the amounts needed are within the expertise of those skilled in the art.

As set out above, the present invention provides a mixture of 4- and 5-substituted regioisomers of 1,2,3-triazole moieties with at least one remote polymerizable moiety. The invention also provides an adhesive, coating, encapsulation, personal care, oilfield, membrane, agricultural, or cleaning composition comprising a mixture of 4- and 5-substituted regioisomers of 1,2,3-triazole moieties with at least one remote polymerizable moiety.

In one embodiment, the present invention provides a mixture of 4- and 5-substituted regioisomers of 1,2,3-triazole moieties with at least one remote polymerizable moiety including compounds represented by the structures:

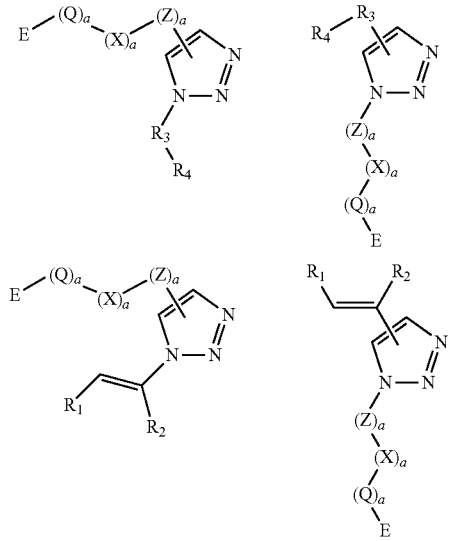

-continued

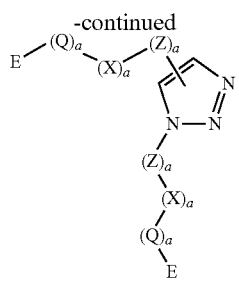

wherein E is a remote polymerizable reactant moiety independently selected from the group consisting of anhydrides, vinyl amides, acrylates, styrenes, maleimides, maleates, fumarates, cinnamyls, vinyl imidazoles, vinyl pyridines, vinyl acetates, acrylamides, vinyl sulfones, vinyl carbonates, vinyl silanes, vinyl actylamides, allyl derivatives, vinyl ethers, epoxies, oxetanes, benzoxazines, oxazolines, and mixtures thereof; Q and Z are independently selected from the group consisting of functionalized and unfunctionalized alkyl, cycloalkyl, alkenyl, and aryl groups, wherein any of the before mentioned groups may be with or without heteroatoms, and mixtures thereof; X is a linker group selected from the group consisting of carbamates, ureas, amides, esters, ethers, ketones, amines, sulfides, disulfides, thiocarbamates, and mixtures thereof; a is 0 or 1; $R_1$, $R_2$, and $R_3$ are independently selected from the group consisting of hydrogen, functionalized and unfunctionalized alkyl, cycloalkyl, alkenyl, and aryl groups, wherein any of the before mentioned groups may be with or without heteroatoms; and $R_4$ is selected from the group consisting of a direct bond, carboxylic acids, esters, amides, anhydrides, aldehydes, ketones, ethers, amines, alcohols, thiols, and mixtures thereof, with the proviso that when $R_3$ is hydrogen, $R_4$ is a direct bond.

As set out above, Q and Z are independently selected from the group consisting of functionalized and unfunctionalized alkyl, cycloalkyl, alkenyl, and aryl groups, wherein any of the before mentioned groups may be with or without heteroatoms, and mixtures thereof. Preferably, Q and Z are independently selected from the group consisting of functionalized and unfunctionalized alkyl groups.

As set out above, X is a linker group selected from the group consisting of carbamates, ureas, amides, esters, ethers, ketones, amines, sulfides, disulfides, thiocarbamates, and mixtures thereof. Preferably, X is selected from the group consisting of carbamates, esters, and ethers, and mixtures thereof.

As set out above, a is 0 or 1, preferably each "a" is not 0 at the same time, more preferably a is 1.

As set out above, $R_1$, $R_2$, and $R_3$ are independently selected from the group consisting of hydrogen, functionalized and unfunctionalized alkyl, cycloalkyl, alkenyl, and aryl groups, wherein any of the before mentioned groups may be with or without heteroatoms. Preferably, $R_1$, $R_2$, and $R_3$ are independently selected from the group consisting of functionalized and unfunctionalized alkyl groups.

As set out above, $R_4$ is selected from the group consisting of a direct bond, carboxylic acids, esters, amides, anhydrides, aldehydes, ketones, ethers, amines, alcohols, thiols, and mixtures thereof, with the proviso that when $R_3$ is hydrogen, $R_4$ is a direct bond. Preferably, $R_4$ is selected from the group consisting of carboxylic acids, amines, alcohols, thiols, and mixtures thereof.

In a preferred embodiment, the mixture is represented by the structure:

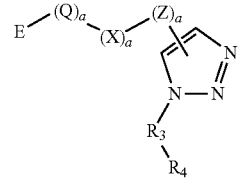

wherein E, Q, Z, X, a, and $R_3$-$R_4$ are as defined above.

In another preferred embodiment, the mixture is represented by the structure:

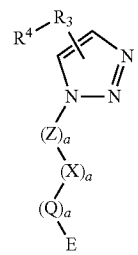

wherein E, Q, Z, X, a, and $R_3$-$R_4$ are as defined above.

In another preferred embodiment, the mixture is represented by the structure:

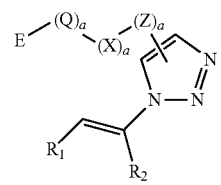

wherein E, Q, Z, X, a, and $R_1$-$R_2$ are as defined above.

In another preferred embodiment, the mixture is represented by the structure:

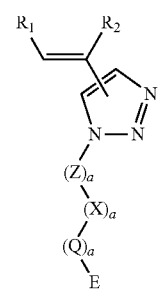

wherein E, Q, Z, X, a, and $R_3$, $R_2$ are as defined above.

In another preferred embodiment, the mixture is represented by the structure:

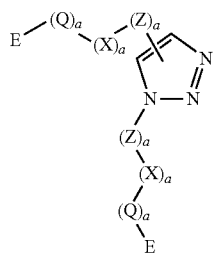

wherein E, Q, Z, X, and a are as defined above.

As set out above, the mixtures of 4- and 5-substituted regioisomers may be separated by conventional chromatographic methods to provide the purified 4-substituted regioisomers and the 5-substituted regioisomers. The purified 4-substituted regioisomers and the 5-substituted regioisomers may then be employed to prepare 4-substituted and 5-substituted homopolymers and non-homopolymers The present invention also provides a 4-substituted 1,2,3-triazole moiety with at least one remote polymerizable moiety. The invention also provides an adhesive, coating, encapsulation, personal care, oilfield, membrane, agricultural, or cleaning composition comprising a 4-substituted 1,2,3-triazole moiety with at least one remote polymerizable.

In one embodiment, the moiety is selected from the group of compounds represented by the structure:

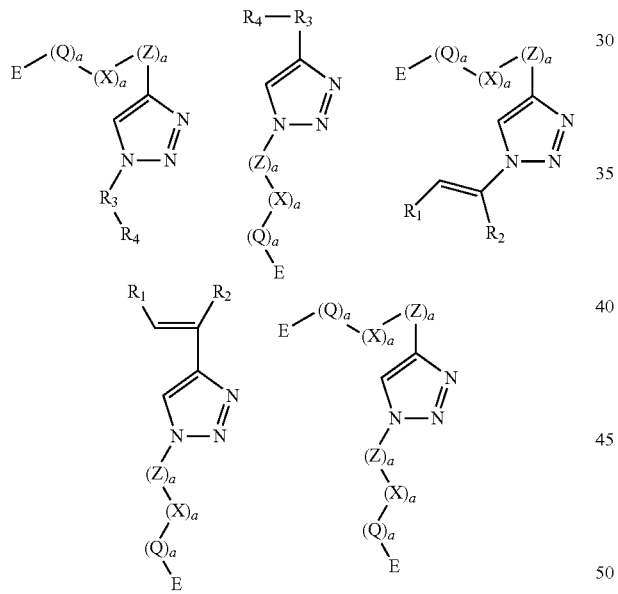

wherein E, Q, Z, X, a, and $R_1$-$R_4$ are as defined above.

In a preferred embodiment, the moiety is represented by the structure:

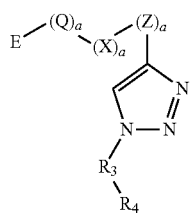

wherein E, Q, Z, X, a, and $R_3$-$R_4$ are as defined above.

In another preferred embodiment, the moiety is represented by the structure:

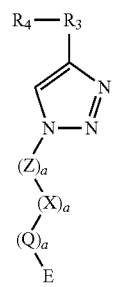

wherein E, Q, Z, X, a, and $R_3$-$R_4$ are as defined above.

In another preferred embodiment, the moiety is represented by the structure:

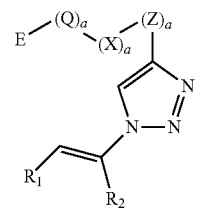

wherein E, Q, Z, X, a, and $R_1$-$R_2$ are as defined above.

In another preferred embodiment, the moiety is represented by the structure:

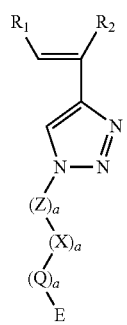

wherein E, Q, Z, X, a, and $R_1$-$R_2$ are as defined above.

In another preferred embodiment, the moiety is represented by the structure:

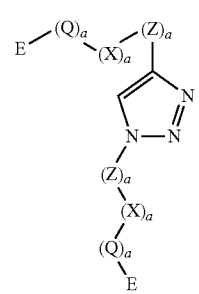

wherein E, Q, Z, X, and a are as defined above.

The present invention also provides a 5-substituted 1,2,3-triazole moiety with at least one remote polymerizable moiety. The invention also provides an adhesive, coating, encapsulation, personal care, oilfield, membrane, agricultural, or cleaning composition comprising a 5-substituted 1,2,3-triazole moiety with at least one remote polymerizable.

In one embodiment, the moiety is selected from the group of compounds represented by the structure:

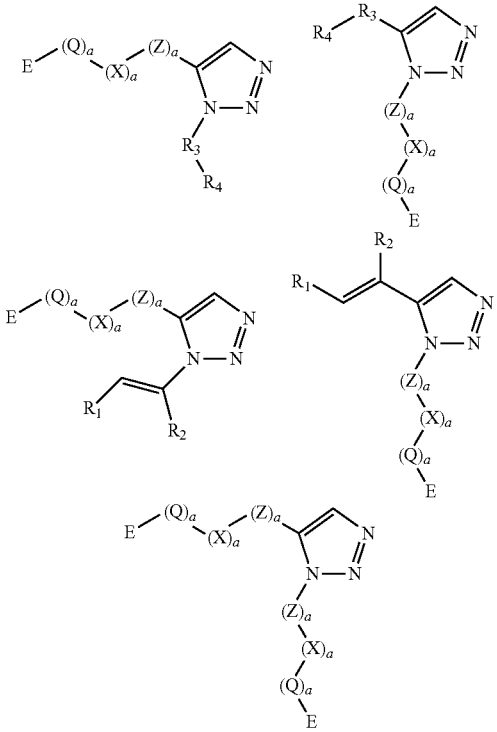

wherein E, Q, Z, X, a, and $R_1$-$R_4$ are as defined above.

In a preferred embodiment, the moiety is represented by the structure:

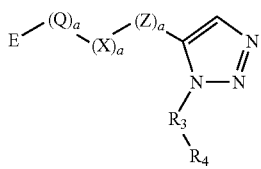

wherein E, Q, Z, X, a, and $R_3$-$R_4$ are as defined above.

In another preferred embodiment, the moiety is represented by the structure:

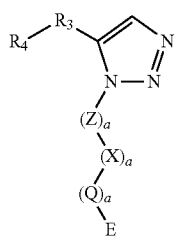

wherein E, Q, Z, X, a, and $R_3$-$R_4$ are as defined above.

In another preferred embodiment, the moiety is represented by the structure:

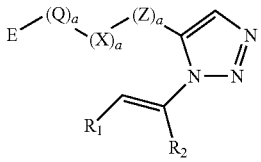

wherein E, Q, Z, X, a, and $R_1$-$R_2$ are as defined above.

In another preferred embodiment, the moiety is represented by the structure:

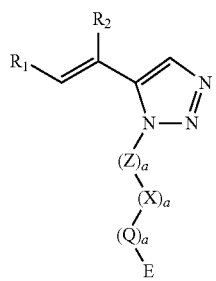

wherein E, Q, Z, X, a, and $R_1$-$R_2$ are as defined above.

In another preferred embodiment, the moiety is represented by the structure:

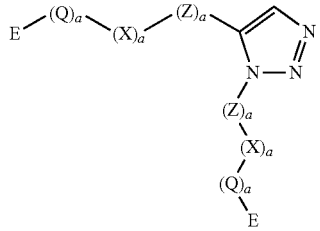

wherein E, Q, Z, X, and a are as defined above.

As set out above, the mixtures of 4- and 5-substituted regioisomers can be separated by chromatography to provide the purified 4- and 5-substituted 1,2,3-triazole moieties. The novel mixtures of 4- and 5-substituted regioisomers of 1,2,3-triazole moieties, and the purified 4- and 5-substituted 1,2,3-triazole moieties, with at least one remote polymerizable moiety, can be converted to a wide variety of useful homopolymers. Depending upon the nature of the remote polymerizable moiety, the presence of a second remote polymerizable moiety or a non-remote polymerizable moiety, the reaction conditions, as well as other factors, the number and type of homopolymers can be varied. For example, when two polymerizable moieties are present in the 1,2,3-triazole moiety, one or both moieties may be polymerized. The novel homopolymers may be employed in a wide variety of compositions, the types of which have been set out above.

Similarly, the novel mixtures of 4- and 5-substituted regioisomers of 1,2,3-triazole moieties, and the purified 4- and 5-substituted 1,2,3-triazole moieties, with at least one remote polymerizable moiety, can be reacted with a comonomer moiety (different polymerizable reactant moiety), to provide a wide variety of useful non-homopolymers. The non-homopolymer may be a random, blocked, or alternating polymer. Depending upon the nature of the comonomer moiety and the remote polymerizable moiety, the presence of a second remote polymerizable moiety or a non-remote polymerizable moiety, the reaction conditions, as well as other factors, the number and type of non-homopolymers can be varied. For example, when two polymerizable moieties are present in the 1,2,3-triazole moiety, or more than one polymerizable moiety is present in the comonomer moiety, one or many moieties may be polymerized. More than one comonomer moiety may also be present in the 1,2,3-triazole moieties in which case, each comonomer moiety may be selected independently. The novel non-homopolymers may be employed in a wide variety of compositions, the types of which have been set out above.

Each comonomer moiety may be independently selected from the group consisting of anhydrides, vinyl amides, acrylates, styrenes, maleimides, maleates, fumarates, cinnamyls, vinyl imidazoles, vinyl pyridines, vinyl acetates, acrylamides, vinyl sulfones, vinyl carbonates, vinyl silanes, vinyl acrylamides, allyl derivatives, vinyl ethers, epoxies, oxetanes, benzoxazines, oxazolines, and mixtures thereof.

The compounds of the present invention can be prepared according to the examples set out below. The examples are presented for purposes of demonstrating, but not limiting, the preparation of the compounds and compositions of this invention.

EXAMPLES

In accordance with the present invention, the following examples are provided to illustrate preferred methods for preparing novel methods for the ligation of azides and alkynes using 1,3-dipolar cycloaddition reactions to provide a functionalized mixture of 4- and 5-substituted regioisomers of 1,2,3-triazole monomers, with at least one remote polymerizable moiety.

Example 1

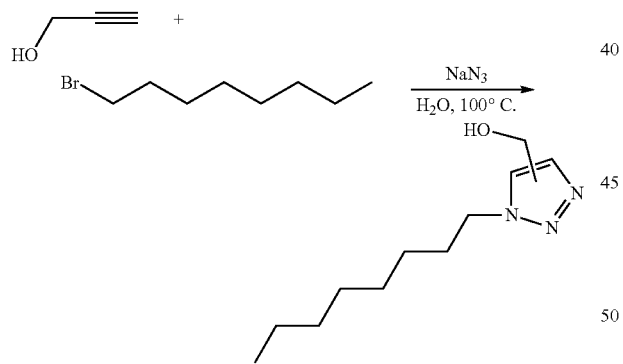

A 500-mL round bottom, 4-neck reaction flask equipped with mechanical stirrer, air supply, oil bath with temperature probe and controller, and reflux condenser was charged with water (103.0 g). With mixing, sodium azide (25.0 g, 0.3845 mol), bromooctane (67.49 g, 0.3495 mol) and propargyl alcohol (5.2 g) were added. The flask was then purged continuously with air to sweep hydrazoic acid gas out of the flask as it formed, and the purge was maintained during the reaction. The reaction was heated at reflux for 25 hours within a temperature range of 100° C.-104° C. The conversion of bromooctane was monitored by gas chromatography (GC) by normalizing reactant area pA* values by the product pA* areas. Aliquats of propargyl alcohol were added during the first six hours of refluxing; after 2 hours into the reaction 5.2 g were added followed by 5.2 g each at 3, 4, 5, and 6 hours. At the end of 25 hours of refluxing, the reaction emulsion was transferred to a separatory funnel. Water (500 mL) was added and the contents were mixed well. An aqueous saturated brine of NaCl (200 mL) was added to promote emulsion phase separation. After 1.5 hours, two phases formed; a dark gold top phase and a cloudy yellow bottom phase. The bottom aqueous phase was discarded. The top organic phase was charged to a 500-mL, 4-neck, round bottom flask equipped with mechanical mixer. Hexane (50 mL) and water (50 mL) were added to the flask and the contents were mixed well (at 500 rpm) mechanically for 40 minutes. The resulting emulsion was then transferred back to the separatory funnel where it was left to phase separate; brine (50 mL) was added to aid in separation. Three phases eventually formed (top=colorless hexane, middle=product dark, bottom=aqueous cloudy yellow). Top and bottom phases were discarded and the dark middle layer was collected. The middle layer was stripped of water at 80° C. on the roto-evaporator. Three shots of water (10 mL each) were added to the product phase and stripped off sequentially at 95° C. over 2.5 hours. The product phase was next added to a 4-neck, round bottom flask charged with 250 mL hexane and mixed well overnight. The hexane layer was decanted off (no product in hexane detected by GC). Solids were filtered out resulting in a phased out oil/hexane mix and light colored crystals. The solids were dissolved in 250 mL of ethyl acetate and the resulting clear gold solution was added to the oil/hexane mix. Then, the resulting solution (300 mL) was washed with 300 mL brine by mechanically mixing in a flask for 30 minutes. The mix phased separated quickly. The top organic phase (EtOAc+product) was collected and charged to a round bottom flask. Silica gel (70 grams) was added and the mixture was mixed rigorously for 30 minutes. The mix was filtered resulting in a clear gold solution. The solution was stripped of solvent leaving a clear gold oil. A total of 47 g of product was collected, representing a 60% yield.

The oil slowly organized to a soft gold crystalline solid that exhibited melting points of 17° C. and 37° C.; thereby, suggesting two isomeric forms. NMR results (FIG. 1) confirmed that the product comprised 60 mole % of 1-octyl-4-(hydroxymethyl)-1,2,3 triazole, and 40 mole % of the 1-octyl-5-(hydroxymethyl)-1,2,3 triazole.

Example 2

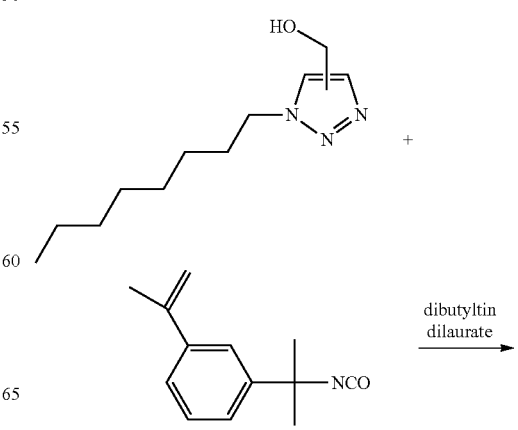

-continued

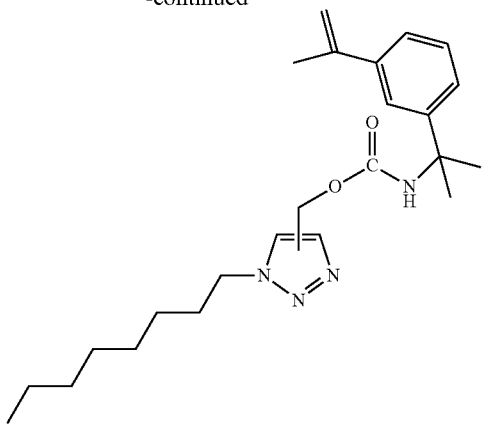

A 250-mL round bottom, 4-neck reaction flask equipped with mechanical stirrer, oil bath with temperature probe and controller, and reflux condenser with bubbler was charged with mixture of 1-octyl-4-(hydroxymethyl)-1,2,3 triazole and 1-octyl-5-(hydroxymethyl)-1,2,3 triazole regioisomers from Example 1(20.0 g, 0.0880 mol) and two drops of dibutyltin dilaurate. With mixing, the flask contents were heated in the oil bath to 70° C.-75° C. This reaction temperature was maintained during the 75-minute addition of isocyanate m-TMI (18.77 g, 0.0880 mol) via slow addition funnel. Following the addition, the reaction temperature was increased to 75° C.-80° C. and held for 3 hours with mixing. The reaction was monitored by observing the exhaustion of the FT-IR isocyanate peak at 2255 cm$^{-1}$. With the disappearance of the peak after 3 hours, this reaction was considered complete. The viscous dark amber oil was bottled while hot for ease in handling.

NMR results confirmed the identity of the product.

Example 3

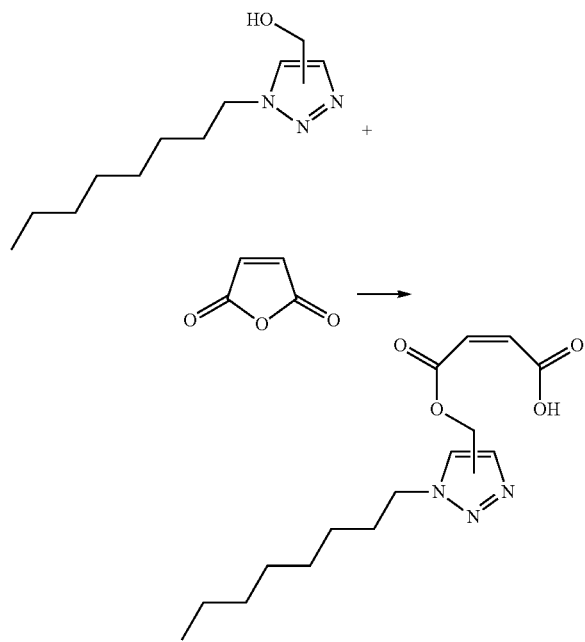

Maleic anhydride (43.15 g, 0.4400 mol) and the mixture of 1-octyl-4-(hydroxymethyl)-1,2,3 triazole and 1-octyl-5-(hydroxymethyl)-1,2,3 triazole regioisomers from Example 1 (100 g, 0.4400 mol) were charged to a 250-mL round bottom, 4-neck reaction flask equipped with a mechanical stirrer, bubbler, and oil bath with a temperature probe and controller. The flask was heated in an oil bath to 85° C. reaction temperature and mixed (200 rpm) for 7 hours. Initially, a minor exotherm (3° C.) developed with some foaming, but the temperature during the final 6 hours of the reaction time ranged between 83° C.-85° C. During this time, the appearance of the reaction changed from a dark brown solution to a dark rust-red oil. When the reaction was complete, the reaction was discharged hot into a storage container for ease in handling.

NMR results confirmed the identity of the product.

Example 4

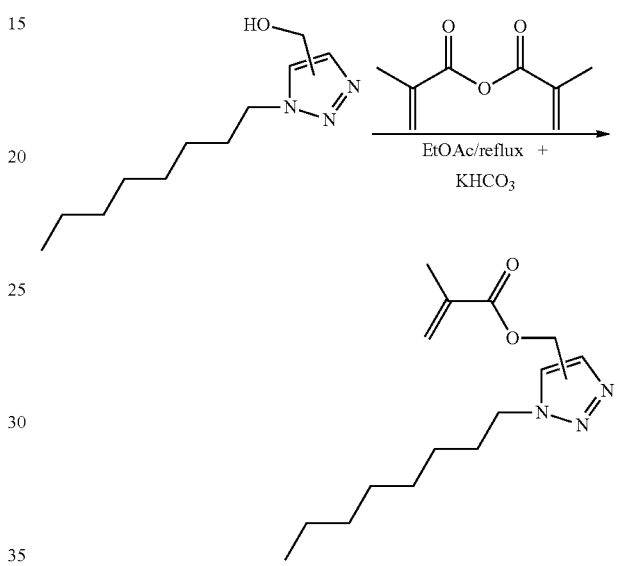

Ethyl acetate (300 mL) and the mixture of 1-octyl-4-(hydroxymethyl)-1,2,3 triazole and 1-octyl-5-(hydroxymethyl)-1,2,3 triazole regioisomers from Example 1 (30 grams) were combined in a 1-L, 4-neck round-bottom flask equipped with a mechanical mixer, thermometer, reflux condenser with bubbler, oil bath, temperature controller and temperature probe. With mixing, the flask was heated in a preheated 86° C. oil bath to a flask contents temperature of 72° C.-74° C. Then, freshly distilled methacrylic anhydride (34.4 g) was added and mixing and heating were continued for a "hold" period of one hour. The first 34.2 g of KHCO$_3$ were added in three lots of 11.4 g each over a one hour period including a 20 minute "hold" following each add. The conversion of the triazole alcohols to the product was monitored by gas chromatography (GC) by normalizing reactant area pA* values by the product pA* area. The reaction became exothermic and the temperature spiked to 80° C.-81° C. Consequently, addition and hold times were extended. A temperature of 73° C.-78° C. was maintained. Two hours after the first KHCO$_3$ addition, 17.1 g more KHCO$_3$ were slowly added to neutralize residual methacrylic anhydride and methacrylic acid. Within one hour the methacrylic anhydride residual was exhausted. When foaming subsided, the reaction was left to sit over night (for convenience). Heating and mixing were continued until methacrylic acid was not observed via GC, which occurred within an 11-12 hour time period following the first KHCO$_3$ addition. After cooling to room temperature, a heavy load of fine white salts was filtered from the reaction solution. The salts were rinsed well with ethyl acetate resulting in a total reaction solution volume of 400 mL. The hazy gold solution was then charged to a 2-L separatory funnel. An aqueous brine of saturated NaCl (400 mL) was added resulting in two phases. The phases were mixed well and allowed to separate.

Gas pressure build-up was noted upon mixing the two phases, thereby requiring frequent venting. Once phases separated, the aqueous layer was discarded and the organic layer was collected. The organic layer was washed twice more with brine and once with 400 mL saturated sodium bicarbonate. The hazy gold solution was mixed over 20 g of magnesium sulfate for ten minutes and then filtered. Silica gel (50 grams) was added to the cloudy gold solution and the mixture was mixed for one hour. It was then filtered through a 1"-2"pad of silica gel (150 g-200 g) resulting in a clear amber solution. The silica gel was rinsed with ethyl acetate to thoroughly extract product. Hydroquinone (1000 ppm, 0.04 g) was added to inhibit polymerization. Solvent was stripped via roto-evaporator at 55° C.-60° C. to 20 Torr with an air bleed. Dry air was bubbled through the solution over night to remove residual solvent. A total of 31 g of product was collected, representing a 78% yield.

Figure 2:
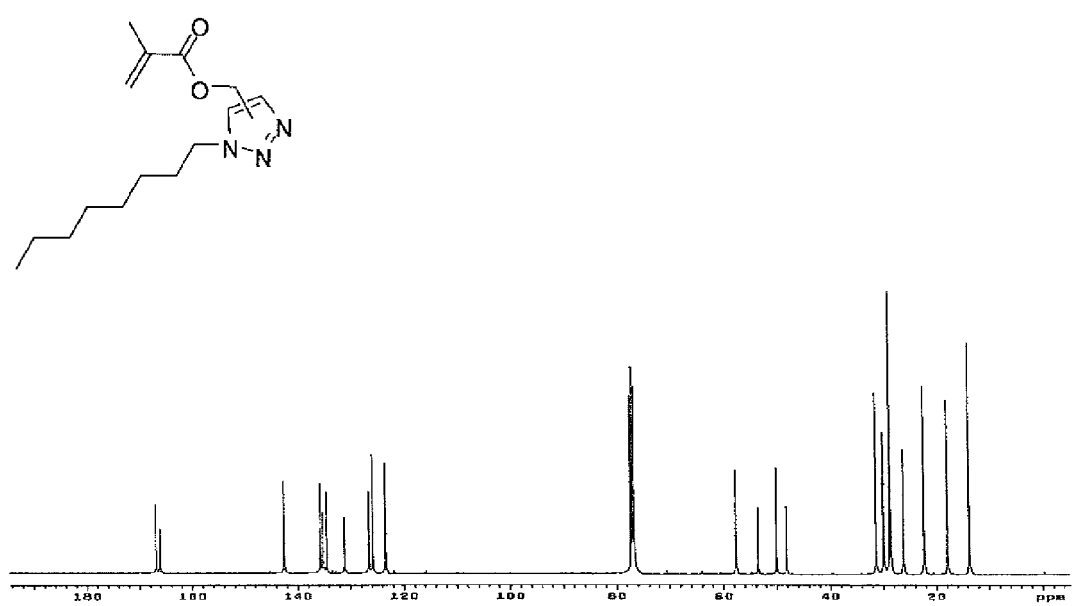
FIG. 2 is an NMR spectrum for compounds produced in accordance with Example 4.

Product was a soft gold solid with a melting point of 26° C. NMR results confirmed the identity of the product (FIG. 2).

Example 5

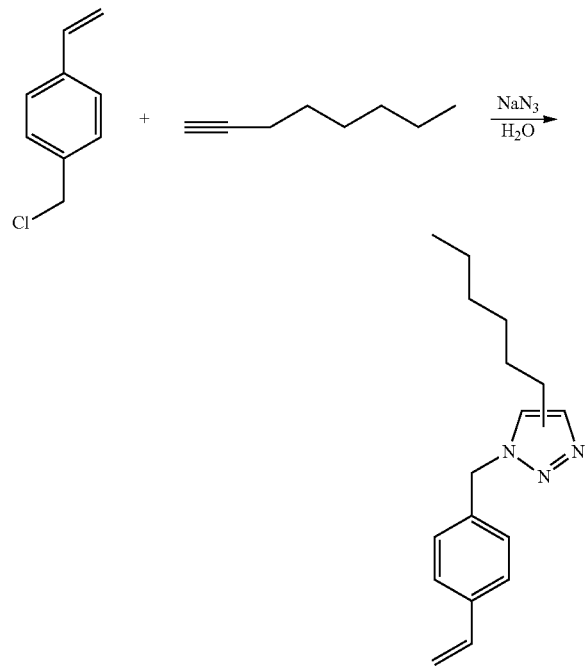

A 500 mL round bottom, 4-neck reaction flask equipped with mechanical stirrer, air supply, oil bath with temperature probe and controller and reflux condenser was charged with water (80.0 g). With mixing, sodium azide (18.74 g, 0.2883 mmol), vinylbenzyl chloride (40.00 g, 0.2621 mol) and 1-octyne (46.2 g, 0.4193 mol) were added. The flask was then purged continuously with air to sweep hydrazoic acid gas out of the flask as it formed. The reaction was heated for 24 hours within a temperature range of 74° C.-77° C. The gold orange slurry was then transferred to a 1-L separatory funnel. Upon cooling to room temperature, 250 mL each of water, brine and hexane were then charged to the funnel and all was mixed well. Upon settling, three separate phases formed in the funnel. The top and bottom phases were discarded. The middle orange phase was collected and dissolved in 250 mL of ethyl acetate, resulting in a hazy red solution. The ethyl acetate solution was then washed with water (3×250 mL each) and passed through a pad of silica gel. Hydroquinone (1000 ppm) was added to the resulting yellow solution. Ethyl acetate was then stripped from the product via roto-evaporation at 60° C. to about 20 Torr. The resulting product was a clear, yellow oil.

NMR results confirmed the identity of the product.

Example 6

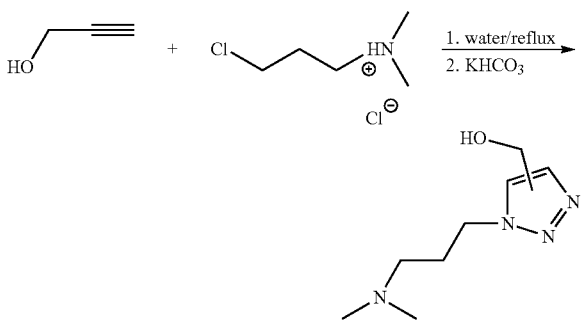

A 2-L, 4-neck round-bottom flask was equipped with a mechanical mixer, thermometer, condenser, air purge and a hot oil bath with temperature probe and controller. An air purge was maintained. Sodium azide (100 g) and water (490 g) were charged to the flask. The azide was fully dissolved before adding the amine (221 g). The amine was then also fully dissolved in the aqueous solution. The solution turned hazy orange with this addition. The oil bath was preheated to 100° C. Propargyl alcohol (15.67 g) was added at t=0. The reaction flask was placed in the hot oil bath with mixing. At reflux, the reaction became a clear orange solution. Refluxing was maintained for 25 hours from this point in time. Throughout the reaction, air flowed through the flask as a purge. The reaction temperature at reflux was maintained at 102° C.-103° C. with the air purge. Over the first hour of refluxing, the reaction solution changed from orange to a clear light gold color. Propargyl alcohol (15.67 g) again was added at 2, 3, 4 and 5 hours after t=0. The color changed to a clear dark amber after refluxing 25 hours. The reaction was transferred to a single-neck two liter round bottom flask, Water, et al. were stripped from the reaction solution on the roto-evaporator at 80° C. and 30 Tarr (final), which resulted in a viscous amber oil containing salt. After cooling, 500 mL of methanol was added to the oil and the mixture was mechanically mixed for 30 minutes. The oil readily dissolved. The methanol et al. were stripped-off on the roto-evaporator at 80° C. and 55 Tarr (final). A viscous amber oil with solids remained. Methanol (500 mL) was added and the mixture was mechanically mixed for 30 minutes. The oil readily dissolved. The salts were filtered and rinsed with methanol. The methanol, et al. were stripped-off on the roto-evaporator at 80° C. and 55 Torr (final). A viscous and hazy amber oil remained. Methanol (300 mL) was added and the mixture was mechanically mixed and chilled in an ice bath. The remaining salts were removed by filtering and the methanol, et al. were stripped off. The resulting product was viscous and amber in color. A total of 219 g was collected, representing a 72% yield of protonated intermediate. A total of 50 g of the intermediate and 250 mL of ethyl acetate were charged to a 1-L, four-neck round bottom flask equipped with mechanical mixer, thermometer and bubbler. The contents were mixed for 30 minutes and a reaction temperature of 28° C.-31° C. was maintained. Next, KHCO$_3$ (125 grams) was added to the mixture at t=0 hours and mixing was continued. At t=4 hours, product was detected via GC, after which a second addition of 125 g of $KHCO_3$ was added. The reaction was mixed overnight, upon which the resulting mixture was a gold-yellow in color. The mixture was filtered to remove salts and the salts were rinsed with ethyl acetate to a total reaction solution volume of 750 mL. The product was a cloudy yellow solution. Magnesium sulfate (40 g) was added to dehydrate the solution, which was then mixed for one hour. The reaction mixture was filtered and the solution stripped at 80° C. and 30 Torr (final). The result was 29 g (58% yield) of a clear gold deprotonated oil product.

Figure 3:
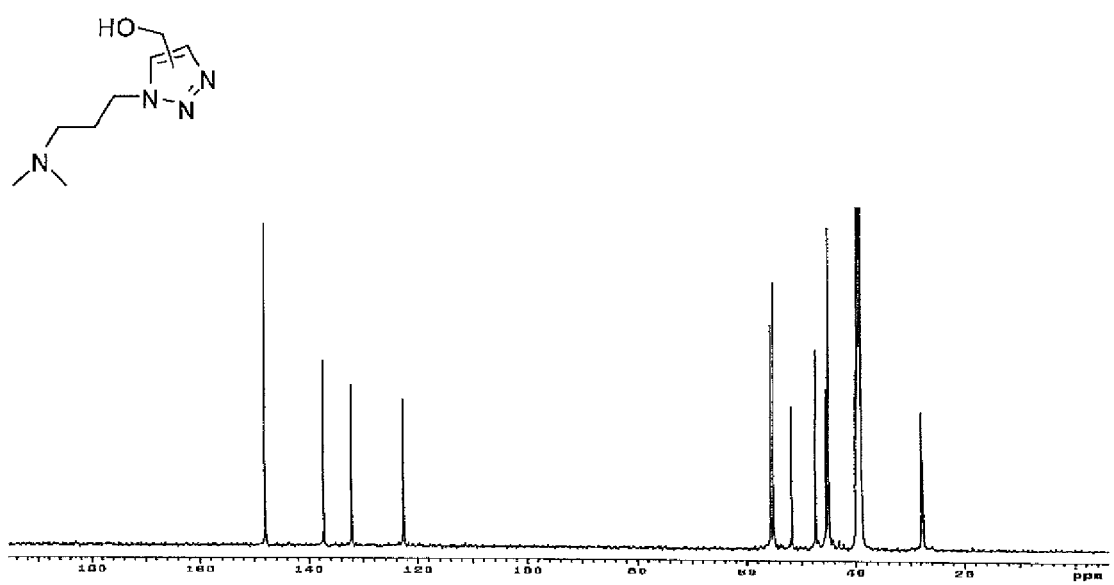
FIG. 3 is an NMR spectrum for compounds produced in accordance with Example 6.

NMR results confirmed the products as 1-(3-(N,N-dimethylamino)propyl-4-(hydroxymethyl)-1,2,3 triazole and 1-(3-(N,N-dimethylamino)propyl-5-(hydroxymethyl)-1,2,3 triazole (FIG. 3).

Example 7

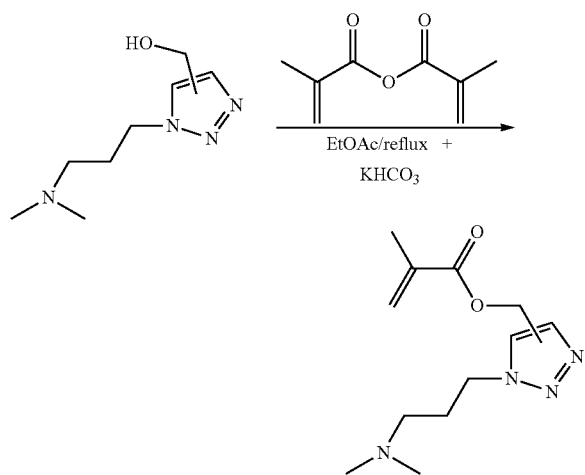

Ethyl acetate (570 mL) and the mixture of 1-(3-(N,N-dimethylamino)propyl-4-(hydroxymethyl)-1,2,3 triazole and 1-(3-(N,N-dimethylamino)propyl-5-(hydroxymethyl)-1,2,3 triazole regioisomers from Example 6 (50.0 grams) were combined in a 1-L, 4-neck round-bottom flask equipped with a mechanical mixer, thermometer, reflux condenser, oil bath, temperature controller and temperature probe. The oil bath was preheated to 86° C. With mixing, the flask was heated in the 86° C. oil bath to a flask contents temperature of 72° C.-74° C. Next, methacrylic anhydride (63.9 grams) was added and mixing and heating were continued for a "hold" period of one hour. The first 66.4 g of $KHCO_3$ were added in three lots of about 22.1 g each over a one hour period including a 20 minute "hold" following each add. The conversion of the dimethylaminopropyl triazole methanol regioisomers to the methacrylate products was monitored by gas chromatography (GC) by normalizing reactant area pA* values by the product pA* area. The reaction became exothermic and the temperature spiked to 80° C.-81° C. Consequently, addition and hold times were extended to maintain a reaction temperature of 77° C.-79° C. Two hours after the last $KHCO_3$ addition, 33.2 g more $KHCO_3$ were slowly added to neutralize residual methacrylic anhydride and methacrylic acid. After foaming subsided, the reaction was left to sit overnight (for convenience). Heating and mixing were continued until methacrylic anhydride and methacrylic acid were not observed via GC. Exhaustion of the anhydride and acid occurred within an 8 hour-8.5 hour time period following the first $KHCO_3$ addition. Upon completion, the reaction was cooled to room temperature and a heavy load of fine white salts was filtered from the reaction solution. The salts were rinsed well with ethyl acetate, resulting in a total reaction solution volume of 600 mL. The hazy deep gold solution was then charged to a 2-L separatory funnel. Saturated $NaHCO_3$ solution (250 mL) was added, resulting in two phases. The phases were mixed well and allowed to separate to an organic gold solution on top and a light yellow aqueous bottom solution. During mixing of the two phases the gas pressure increased, and thus frequent venting was required. Upon phase separation, the organic fraction was isolated in an Erlenmeyer flask. Magnesium sulfate (20 g) was added and the mixture mixed for 30 minutes. The solids were removed by filtration, leaving a clear gold solution. Silica gel was added with vigorous mixing for one hour via magnetic spin bar. The mixture was then filtered through a 1"pad of silica gel (about 150-200 g) resulting in a clear light yellow solution. The filtered silica gel was rinsed with ethyl acetate to thoroughly extract product. Hydroquinone (1000 ppm based on theoretical yield) was added to the solution to inhibit polymerization and solvent was stripped via roto-evaporator at 45° C.-50° C. with an air bleed. Dry air was bubbled through the solution over night to remove residual solvent. Product is a clear gold oil. A total of 25 g of product was collected, representing a 58% yield. Product was stored in a refrigerator in an opaque brown plastic bottle.

Figure 4:
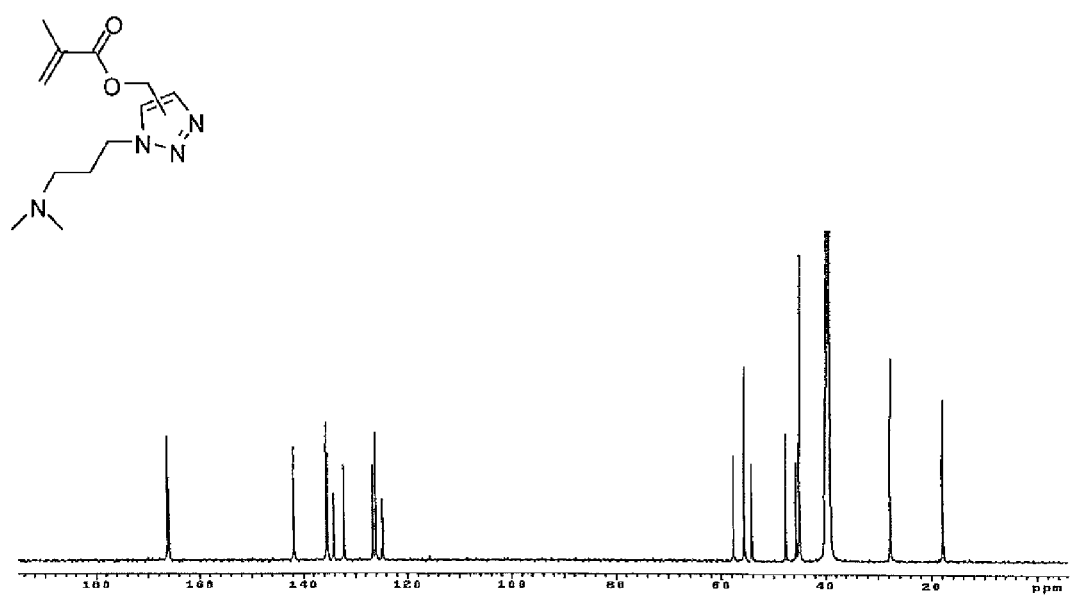
FIG. 4 is an NMR spectrum for compounds produced in accordance with Example 7

NMR results confirmed the products as 1-(3-(N,N-dimethylamino)propyl-4-(methacryloyloxy)-1,2,3 triazole and 1-(3-(N,N-dimethylamino)propyl-5-(methacryloyloxy)-1,2,3 triazole (FIG. 4).

While a number of embodiments of this invention have been represented, it is apparent that the basic construction can be altered to provide other embodiments that utilize the invention without departing from the spirit and scope of the invention. All such modifications and variations are intended to be included within the scope of the invention as defined in the appended claims rather than the specific embodiments that have been presented by way of example.

I claim:
1. A mixture of 4- and 5-substituted regioisomers of 1,2,3-triazole moieties with at least one remote polymerizable moiety, wherein said mixture is selected from the group consisting of:

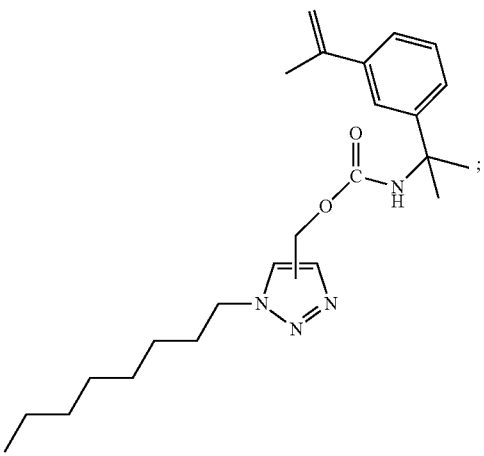

27
-continued
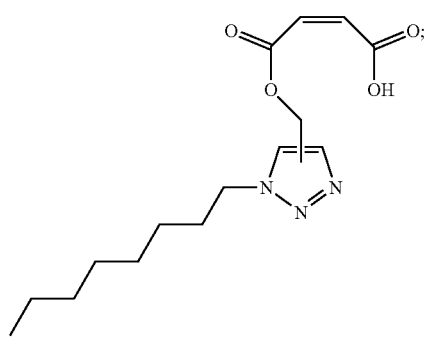
28
-continued
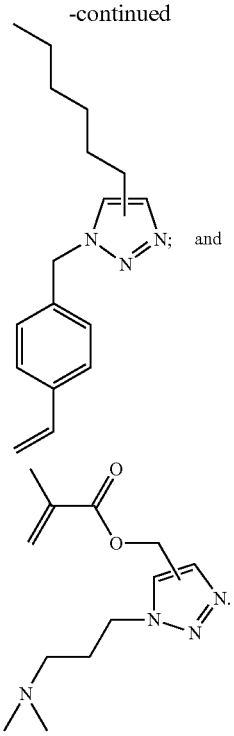
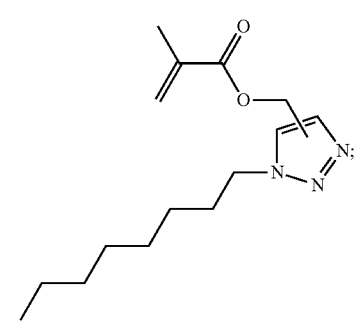
* * * * *